United States Patent
Kolter et al.

[11] Patent Number: 6,066,334
[45] Date of Patent: May 23, 2000

[54] USE OF REDISPERSIBLE POLYMER POWDERS OR POLYMER GRANULES AS BINDERS FOR PRODUCING SOLID PHARMACEUTICAL PRESENTATIONS

[75] Inventors: Karl Kolter, Limburgerhof; Kristin Tiefensee, Westheim; Katrin Zeitz, Ludwigshafen, all of Germany

[73] Assignee: BASF Aktiengesellschaft, Ludwigshafen, Germany

[21] Appl. No.: 09/037,796

[22] Filed: Mar. 10, 1998

[30] Foreign Application Priority Data

Mar. 10, 1997 [DE] Germany .......................... 197 09 663

[51] Int. Cl.⁷ .............................. A61K 9/14; A61K 47/32
[52] U.S. Cl. ...................... 424/465; 424/501; 574/772.3
[58] Field of Search ........................ 514/772.3; 424/501, 424/465

[56] References Cited

U.S. PATENT DOCUMENTS 5,252,704 10/1993 Bright et al. .
5,490,990 2/1996 Grabowski et al. .
5,705,553 1/1998 Kuropka .................................. 524/459

FOREIGN PATENT DOCUMENTS 2727976 9/1994 France .
43 41 156 12/1993 Germany .
WO98/42772 10/1998 WIPO .

*Primary Examiner*—Peter F. Kulkosky
*Attorney, Agent, or Firm*—Keil & Weinkauf

[57] ABSTRACT

Redispersible polymer powders or polymer granules consisting of
a) 10–95% by weight of polyvinyl acetate,
b) 5–90% by weight of an N-vinylpyrrolidone-containing polymer,
c) 0–20% by weight of another water-soluble or water-swellable substance and
d) 0–20% by weight of a water-insoluble dusting agent with or without
e) other additives,
are used as binders for producing solid pharmaceutical presentations, where the binder content in the presentation is from 0.5 to 20% by weight.

6 Claims, No Drawings

USE OF REDISPERSIBLE POLYMER POWDERS OR POLYMER GRANULES AS BINDERS FOR PRODUCING SOLID PHARMACEUTICAL PRESENTATIONS

The present invention relates to the use of redispersible polymer powders or polymer granules consisting of polyvinyl acetate and N-vinylpyrrolidone-containing polymers as binders for producing solid pharmaceutical presentations.

In order to be able to deliver drugs to their site of action, it is necessary to put them in the form suitable for the physiological characteristics of the site of administration and the physicochemical properties of the active ingredient. Only in rare cases is administration possible without any forming, ie. as single dose containing only the active ingredient. As a rule, conversion of the active ingredients into suitable drug forms is possible only by the use of ancillary substances.

However, both active ingredients and ancillary substances, such as bulking agents, often have very poor binding capacity so that the use of additional binders for producing a solid presentation is unavoidable. The amount and nature of the binder, but also the processing method, crucially influence the properties of solid presentations, eg. those of granules, such as particle size, flowability, compressibility, dust formation, porosity or surface structure, and the properties of compacts produced therefrom, such as breaking resistance, friability, disintegration and release of the active ingredient.

In pharmaceutical technology, a distinction is made, depending on the processing method, between wet and dry binders. The latter are used inter alia in direct tableting and in dry granulation or compaction. In these cases, the binder is mixed with the active ingredient and, where appropriate, other ancillary substances and then tableted directly or granulated or compacted. Dry binders must display a certain plasticity under pressure because this enlarges the areas of contact between binder and active ingredient or ancillary substance particles so that the adhesive forces increase and, as a consequence, stronger granules or a stronger tablet result(s).

In contrast to this, in wet granulation the active ingredient/ancillary substance mixture is moistened with a solution of the binder in water or an organic solvent, and the moist composition is forced through a screen and then dried. Moistening and drying can moreover take place in parallel, for example in fluidized bed granulation.

For optimal processing, the binder should form a low-viscosity solution because viscous solutions result in inhomogeneous granules.

Because of the fact that the disintegration of the drug forms and the rate of release of the active ingredients ought to be negligibly influenced by the binder, only water-soluble binders are currently used in the market for instant release forms.

Examples of widely used binders are polyvinylpyrrolidone, vinyl acetate/vinylpyrrolidone copolymers, gelatin, starch pastes, maltodextrins, hydroxyalkylated and carboxyalkylated cellulose derivatives such as hydroxypropylmethylcellulose, methylcellulose, sodium carboxymethylcellulose, and types of natural gums such as gum arabic, pectin or alginate.

Many of these binders have a high viscosity in solution and are difficult to process. All these binders lack the required plasticity which is important in wet granulation but especially in direct tableting or compaction. The mechanical stability of the granules and tablets produced with a binder increases with its plasticity.

U.S. Pat. No. 5,252,704 describes the production of redispersible polymer powders using polyvinylpyrrolidone as dispersing auxiliary. The stated area of use is in the manufacture of cement. On the other hand, pharmaceutical applications are not mentioned.

DE-B-4341156 describes the use of polymer dispersion powders which are dispersible in water and have a core/shell structure and pharmaceutical carriers in drug forms with delayed release of active ingredient, the content of dispersion powder in the tablet being more than 75% by weight.

DE-A-4220782 describes processes for producing delayed release solid pharmaceutical forms by application of a binder to a core containing active ingredient. The binders used in this case are (meth)acrylate-based polymers.

It is an object of the present invention to find polymer powders or polymer granules consisting of a water-insoluble and water-soluble polymer which are suitable as binders for producing solid pharmaceutical presentations, where the binder content in the presentation is to be less than 20% by weight. The presentations produced in this way should, furthermore, make rapid release of the active ingredients possible.

We have found that this object is achieved by the use of redispersible polymer powders or polymer granules consisting of
a) 10–95% by weight of polyvinyl acetate,
b) 5–90% by weight of an N-vinylpyrrolidone-containing polymer,
c) 0–20%. by weight of another water-soluble or water-swellable substance and
d) 0–20% by weight of a water-insoluble dusting agent with or without
e) other additives,
as binders for producing solid pharmaceutical presentations, where the binder content in the presentation is from 0.5 to 20% by weight.

It has now been found, surprisingly, that polymer powders or polymer granules consisting of polyvinyl acetate and N-vinylpyrrolidone-containing polymers, especially polyvinylpyrrolidone and vinyl acetate/vinylpyrrolidone copolymers or mixtures thereof, have excellent binding effects and, moreover, have a negligible influence in concentrations in the range from 0.5 to 20% of the total weight of the formulation on the disintegration and the release of active ingredient. The latter would have been expected because of the introduction of a water-insoluble polymer such as polyvinyl acetate.

The two polymers ideally complement one another. Polyvinylpyrrolidone has excellent solubility in water and very good hydrophilizing and stabilizing capacity for active ingredients and improves dissolution of active ingredients in body fluids. Polyvinyl acetate is insoluble in water and has not to date been described as binder. It was only by combining with polyvinylpyrrolidone or with vinyl acetate/vinylpyrrolidone copolymers that this application became possible. Polyvinyl acetate markedly increases the plasticity in the final product. The two polymers are not miscible with one another—as proven by DSC investigations—so that simple combination, for example by a homogeneous melt, is not possible. It has additionally been found that for good binding activity the polyvinyl acetate must be very finely distributed in the product.

The redispersible polymer powders are produced by initial emulsion polymerization of vinyl acetate, then addition of the N-vinylpyrrolidone-containing polymer, with or without other ancillary substances, to the resulting shear-stable and fine-particle dispersion, and spray-drying of the mixture.

Examples of preferred N-vinylpyrrolidone-containing polymers are polyvinylpyrrolidone and vinyl acetate/vinylpyrrolidone copolymers.

The K values of the polymers should be in the range from 10 to 350, preferably 30 to 150, particularly preferably in the range from 50 to 90. The K value required in each case can be adjusted in a conventional way by the choice of the polymerization conditions, for example the polymerization time and the initiator concentration. The K values are measured by the method of Fikentscher, Cellulosechemie, 13 (1932) 58–64 and 71–74, at 25° C. in 0.1% by weight aqueous solution.

Addition of fine-particle, water-insoluble spraying aids during the spray drying is able to prevent adhesion of the particles formed. It is particularly advantageous in this connection for these spraying aids to be atomized into the spray dryer. However, it is also possible to add the spraying aids to the dispersion before spraying, or to mix them in only after the spray-drying to prevent the particles caking together. Dusting agents which can be used are up to 20% by weight, based on the solids content, of fine-particle water-insoluble substances, in particular at least one representative from the group of cellulose, preferably microcrystalline cellulose, disperse silica, talc, bentonite, magnesium stearate or a calcium phosphate.

The emulsion polymerization is carried out in a conventional way at from 50° C. to 95° C., preferably from 60° C. to 80° C., in the presence of known polymerization initiators.

Suitable and preferred polymerization initiators are free-radical formers, for example peroxides such as, preferably peroxosulfates, peroxodisulfates and azo compounds such as azodiisobutyronitrile.

Emulsifiers which can be employed are both ionic and nonionic emulsifiers or mixtures thereof. Their total concentration is from 0.2 to 10% by weight, preferably from 0.4 to 7% by weight, based on the total monomer content. It is furthermore possible to employ as other ancillary substances up to 20% by weight, based on the solids content, of water-soluble or water-swellable protective colloids such as cellulose derivatives, preferably hydroxypropylmethylcellulose, methylcellulose or hydroxyethylcellulose, galactomannan, pectin, xanthan, polyvinyl alcohol, acrylate/methacrylate copolymers, sodium carboxymethyl starch, cellulose, degraded starches, maltodextrins etc. The emulsifying ancillary substances can moreover be added before, during and after the polymerization.

The dispersion has a solids content of from 10 to 45% by weight, preferably from 15 to 35% by weight.

The sedimentation-stable polymer dispersion has average particle sizes of from 0.1 to 7 $\mu$m, preferably from 0.3 to 4 $\mu$m. The determination takes place in a conventional way, eg. by means of an ultracentrifuge, photon correlation spectroscopy or by determining the transmission of light. The particle size is normally controlled by the emulsifier concentration or the temperature.

The shear stability of the polyvinyl acetate dispersion is of crucial importance. Only very shear-stable dispersions are able to form adequately redispersible powders after spraying.

The shear stability is tested by shearing the dispersion using a nopped stirrer at 2000 rpm for 15 min and gravimetric determination of the coagulate after screening through a 125 $\mu$m screen. Shear-stable dispersions have coagulate contents of <0.1%.

The polyvinylpyrrolidone is preferably added as 10 to 50% by weight solution with continuous stirring. Coagulation may occur if added as solid or as more concentrated solution.

The spray drying takes place in a conventional way in spray towers with the dispersion which is to be dried being atomized by nozzles or disks. The hot gas, eg. air or nitrogen, can be fed in cocurrently or countercurrently, with the cocurrent process being particularly preferred because it leads to less temperature stress.

It is also possible to employ FSD (fluidized spray drying) technology, in which initial spray-drying is immediately followed by agglomeration in a fluidized bed. Freeze-drying is an alternative possibility.

The ratio by weight of polyvinyl acetate to polyvinylpyrrolidone or vinyl acetate/vinylpyrrolidone copolymers can vary in the range from 95:5 to 10:90. Ratios from 90:10 to 30:70 are particularly preferred. It is furthermore possible for the products to contain other hydrophilic, water-soluble polymers such as polyvinyl alcohol, hydroxypropylmethylcellulose, hydroxypropylcellulose, methylcellulose, hydroxyethylcellulose, galactomannan, pectin, xanthan, acrylate/methacrylate copolymers, sodium carboxymethyl starch or -cellulose, degraded starches, maltodextrins or else low molecular weight substances such as monosaccharides, disaccharides, sugar alcohols, water-soluble inorganic salts, amino acids, water-soluble acids and their salts or surfactants. These hydrophilic ancillary substances can also be added after the redispersion of a product consisting of polyvinyl acetate and polyvinylpyrrolidone or vinyl acetate/vinylpyrrolidone copolymers to give the binder dispersion. These hydrophilic ancillary substances may exert an additional stabilizing effect on the polyvinyl acetate dispersions and promote rapid release of the active ingredient from the presentation. The use of polyvinyl alcohol and methylhydroxypropylcellulose is particularly preferred.

Additional hydrophilic properties of the redispersible polymer powders according to the invention can be adjusted by using partially hydrolyzed polyvinyl acetate, in which case polyvinyl acetates with a degree of hydrolysis of up to 50 mol % are particularly used.

The polymer powders or polymer granules according to the invention display activities both as dry and as wet binders in granulation and tableting which are distinctly superior to conventional binders. This can be proven by the higher breaking resistances and lower friabilities. The disintegration and release properties of pharmaceutical compositions produced with the products according to the invention do not differ from comparable compositions with conventional binders. In wet granulation, the low viscosity in water proves to be a particular advantage because this allows the binder concentration to be higher. It is thus possible to reduce the granulation times and granulation costs.

For use as wet binder, the product according to the invention is introduced into water with stirring, usually adjusting concentrations of from 5 to 30% by weight. It is then possible to add the described hydrophilic ancillary substances, likewise with stirring. The dispersion is ready for use after a short time and can be used for the purposes of granulation. The binder concentrations in the final product are preferably from 1 to 10% by weight.

For use as dry binder, the product according to the invention is mixed dry with the active ingredient and other ancillary substances, for example bulking agents, flow regulators, disintegrants and lubricants, and compressed or compacted. Normally from 1 to 15% by weight of polymer mixture according to the invention are used. It has been demonstrated that the dry binding activity increases as the concentration of the product according to the invention in the presentation increases.

The abovementioned presentations which contain the polymeric binders according to the invention are preferably solid compositions. By this are meant, inter alia, tablets, microtablets, coated tablets, pastilles, capsules, granules or pellets.

EXAMPLE 1

Preparation of a redispersible powder consisting of about 95% by weight of polyvinyl acetate/polyvinylpyrrolidone in the ratio 80:20 by weight and 5% by weight of polyvinyl alcohol.

500 g of vinyl acetate were emulsified in water with 0.5% by weight of sodium lauryl sulfate under nitrogen in a stirred vessel with reflux condenser and were polymerized by initiation with 0.3% by weight of sodium persulfate at 75° C. After addition of 5% by weight of polyvinyl alcohol (Mowiol® 8-88 from Hoechst), the reaction mixture was cooled to room temperature to result in a dispersion with a solids content of 27% by weight and an average particle size of 1 mm.

The dispersion was mixed with 417 g of a 30% by weight aqueous polyvinylpyrrolidone solution (Kollidon® K 30, from BASF) and the mixture was spray-dried in a cocurrent of nitrogen with an inlet temperature of 140° C. to result in a white, free-flowing powder.

EXAMPLE 2

Determination of the compression properties of polyvinyl acetate/polyvinylpyrrolidone in the ratio 80:20 by weight (K value: 30) compared with polyvinylpyrrolidone (K value: 30).

A mixture of the particular binder and 0.5% by weight magnesium stearate which had been prepared by mixing in a Turbula mixer for 10 minutes was compressed in a Korsch EKO eccentric press to tablets with a diameter of 12 mm and a weight of 300 mg. The tablet press was fully instrumented so it was possible to record force-time and force-travel plots. Further compression parameters were calculated from these data by a software program.

|  | Polymer mixture of 80% by weight polyvinyl acetate and 20% by weight polyvinyl-pyrrolidone | Polyvinyl-pyrrolidone (K value 30) |
| --- | --- | --- |
| Pressure [MPa] | 162 MPa | 160 MPa |
| Compaction resistance | 3.0 | 3.8 |
| Tensile strength [MPa] | 7.41 MPa | 2.44 MPa |

The compaction resistance R is defined as
R=Δ1 g pressure/Δ1 g apparent density.

A lower value of R means less resistance of the material to compression.

The tensile strength is defined as
TS=2×breaking resistance/π×diameter×height.

Higher tensile strength values are characteristic of better mechanical properties.

It emerged that the mixture of polyvinyl acetate and polyvinylpyrrolidone in the ratio 80:20 by weight was more easily compressible than polyvinylpyrrolidone and resulted in considerably greater strengths.

EXAMPLE 3

Use of polyvinyl acetate/polyvinylpyrrolidone in the ratio 80:20 by weight as dry binder in a directly tableted ascorbic acid tablet.

Formula:

| Crystalline ascorbic acid | 200.0 mg |
| --- | --- |
| Ludipress ® (BASF) | 237.5 mg |
| Dry binder consisting of 80% by weight polyvinyl acetate and 20% by weight polyvinylpyrrolidone | 50.0 mg |
| Kollidon ® CL (BASF) | 10.0 mg |
| Magnesium stearate | 2.5 mg |
| Total weight | 500.0 mg |

All the ingredients were forced through a 0.8 mm screen, mixed in a Turbula mixer for 10 minutes and then compressed in a fully instrumented Korsch EKO eccentric press under a force of 18 kN to biplanar, beveled tablets with a diameter of 12 mm and a weight of 500 mg. The compressibility of the mixture was excellent, and it resulted in tablets with the following properties:

| Breaking resistance: | 93N |
| --- | --- |
| Friability: | <0.2% |
| Disintegration: | 1 min |
| Release: (in 900 ml of simulated gastric fluid, 100 rpm) | 98.8% after 30 min |

On use of the same amount of maltodextrin as binder in place of the polyvinyl acetate/polyvinylpyrrolidone combination, the breaking resistance was only 53 N, and it was 68 N in the case of pure polyvinylpyrrolidone (Kollidon® K 30, BASF) and 79 N in the case of a copolymer of vinyl acetate and vinylpyrrolidone (Kollidon® VA 64, BASF).

EXAMPLE 4

Use of a mixture of 8 parts by weight of polyvinyl acetate and 2 parts by weight of vinylpyrrolidone/vinyl acetate copolymer (40:60) and 5% by weight of polyvinyl alcohol as dry binder in a directly tableted ibuprofen tablet.

Formula:

| Ibuprofen | 400.0 mg |
| --- | --- |
| Microcrystalline cellulose (Avicel ® PH 102) | 133.0 mg |
| Dry binder consisting of 8 parts by weight of polyvinyl acetate and 2 parts by weight of vinylpyrrolidone/vinyl acetate copolymer (40:60) and 5% by weight of polyvinyl alcohol | 40.0 mg |
| Kollidon ® CL | 18.0 mg |
| Aerosil ® 200 | 6.0 mg |
| Magnesium stearate | 3.0 mg |
| Total weight | 600.0 mg |

All the ingredients apart from magnesium stearate were forced through a 0.8 mm screen, mixed in a Lödige mixer for 1 minute and, after addition of the magnesium stearate which had likewise been screened, mixed for a further 1 minute. This tableting mixture (batch size: 1.8 kg) was compressed under 80 MPa in a Korsch EKO eccentric press to biplanar beveled tablets with a diameter of 12 mm and a weight of 600 mg.

Properties of the Tablets:

| Tensile strength: | 1.5 MPa |
|---|---|
| Friability: | 0.1% |
| Disintegration: | 1 min |
| Release: (USP method) | 99.5% after 30 min |

EXAMPLE 5

Use of a mixture of 99% by weight of polyvinyl acetate/polyvinylpyrrolidone in the ratio 50:50 by weight and 1% by weight of highly disperse silica as wet binder in a paracetamol tablet.

Formula:

| Paracetamol powder | 150.0 mg |
|---|---|
| Lactose EP D 20 | 155.0 mg |
| Corn starch | 155.0 mg |
| Binder consisting of 99% by weight of polyvinyl acetate/polyvinylpyrrolidone in the ratio 50:50 by weight and 1% by weight of highly disperse silica | 15.0 mg |
| Kollidon ® CL | 22.5 mg |
| Magnesium stearate | 2.5 mg |
| Total weight | 500.0 mg |

3.0 kg of paracetamol powder, 3.10 kg of lactose EP D 20 and 3.10 kg of corn starch were forced through a 0.8 mm screen and mixed in a Diosna mixer for 1 minute. 0.3 kg of the binder consisting of 99% by weight of polyvinyl acetate/polyvinylpyrrolidone 50:50 and 1.0% by weight of highly disperse silica were dispersed by stirring in 900 ml of purified water and slowly introduced into the running Diosna mixer. After the addition, granulation was continued for 2 minutes, the consistency of the granules was tested and the mixer was emptied. The wet granules were dried on a tray at 40° C., returned to a Diosna mixer and, after addition of 0.45 kg of screened Kollidons® CL and 0.05 kg of screened magnesium stearate, mixed for 2 minutes without chopper.

These granules were then compressed under a force of 18 kN in a Korsch PH 106 rotary press to give biplanar beveled tablets with a diameter of 12 mm and a total weight of 500 mg.

Properties:

| Breaking resistance: | 48N |
|---|---|
| Friability: | 0.35% |
| Disintegration: | 1 min |
| Release: (USP method) | 99.1% after 30 min |

The result on use of a maltodextrin (DE 18) as binder in the same amount was only 26 N and with pure polyvinylpyrrolidone (K value 30) was 38 N.

We claim:

1. A solid, rapid release, pharmaceutically active composition, from which the active ingredients are released within a time of from 0.1 to 1 hour, as measured in simulated gastric acid, having a binder consisting essentially of
   a) 10–95% by weight of polyvinyl acetate,
   b) 5–90% by weight of an N-vinylpyrrolidone-containing polymer,
   c) 0–20% by weight of another water-soluble or water-swellable substance and
   d) 0–20% by weight of a water-insoluble dusting agent with or without
   e) ancillary ingredients, selected from the group consisting of bulking agents, flow regulators, disintegrants and lubricants,
   where binder content is from 0.5 to 20% of the total weight and wherein the polymers a) and b) have a K value of from 10 to 350.

2. The solid pharmaceutically active composition of claim 1 wherein component b) is selected from the group consisting of polyvinylpyrrolidone, vinyl acetate/vinylpyrrolidone copolymers and mixtures thereof.

3. The solid pharmaceutically active composition of claim 1 wherein the redispersible polymer powders or polymer granules are processed with the active ingredient by direct tableting, dry granulation or wet granulation.

4. The rapid release, pharmaceutically active composition of claim 1 in the form of redispersible powders or granules consisting essentially of pharmaceutically active ingredients and a binder consisting essentially of
   a) 80% by weight of polyvinyl acetate,
   b) 20% by weight of an N-vinylpyrrolidone-containing polymer, selected from the group consisting of polyvinylpyrrolidone, vinyl acetate/vinylpyrrolidone copolymers and mixtures thereof,
   c) 0–20% by weight of a water-soluble or water swellable substance selected from the group consisting of cellulose derivatives, acrylate/methacrylate copolymers and polyvinyl alcohols or mixtures thereof
   d) 0–20% by weight of a water-insoluble dusting agent selected from the group consisting of cellulose, disperse silica, talc, bentonite, magnesium stearate and calcium phosphate or mixtures thereof
   e) and auxiliary components selected from the group consisting of microcrystalline cellulose, lactose and/or corn starch, wherein the binder content in the said composition is from 0.5 to 20% by weight, resulting in tablets with a friability no greater than 0.35%.

5. The redispersible powders or granules as claimed in claim 4, wherein said binder consists essentially of 95% by weight of polyvinyl acetate/polyvinylpyrrolidone in the ratio 80:20 by weight and 5% by weight of polyvinyl alcohol.

6. The redispersible powders or granules according to claim 4, wherein said binder consists essentially of 95% by weight of polyvinyl acetate/vinylpyrrolidone-vinyl acetate copolymer (40:60) in the ratio 8:2 and 5% by weight of polyvinyl alcohol.

* * * * *